US008980847B2

(12) United States Patent
Kim et al.

(10) Patent No.: US 8,980,847 B2
(45) Date of Patent: Mar. 17, 2015

(54) METHOD FOR TREATING VARICOCELE OR MALE INFERTILITY USING ANTHOCYANIN EXTRACTED FROM BLACK SOYBEAN

(75) Inventors: Sae-Woong Kim, Seongnam (KR); Myung-Hoon Chun, Yongin (KR); In-Beom Kim, Seongnam (KR); U-Syn Ha, Seoul (KR); Su-Jin Kim, Namyangju (KR); Hoon Jang, Daejeon (KR)

(73) Assignee: Catholic University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/435,711

(22) Filed: Mar. 30, 2012

(65) Prior Publication Data
US 2013/0085114 A1 Apr. 4, 2013

(30) Foreign Application Priority Data
Sep. 29, 2011 (KR) .......................... 10-2011-0099358

(51) Int. Cl.
*A61K 31/7048* (2006.01)
*A61K 36/48* (2006.01)
*A23L 1/30* (2006.01)

(52) U.S. Cl.
CPC ........... *A61K 31/7048* (2013.01); *A23L 1/3002* (2013.01); *A61K 36/48* (2013.01)
USPC ........................................................ 514/27

(58) Field of Classification Search
None
See application file for complete search history.

(56) References Cited

FOREIGN PATENT DOCUMENTS

KR    10-2010-0098774    *  9/2010  .............. A23L 1/312

OTHER PUBLICATIONS

Lee et al., KR 10-2010-0098774, Sep. 2010, machine translation, Retreived on May 8, 2013 from http://kposd.kipo.go.kr:8088/up/kpion/.*

Jang et al. The Changes of Testis and the Effects of Anthocyanin on Spermatogenesis in Rat Induced Varicocele. Korean J Androl. vol. 29, No. 1, Apr. 2011 machine translation, Retreived on May 8, 2013 from http://translate.google.com.*
"sitology" in Collins English Dictionary (2000), Retrieved on May 9, 2013 from http://www.credoreference.com/entry/hcengdict/sitology.*
Choung et al. Isolation and Determination of Anthocyanins in Seed Coats of Black Soybean (Glycine max (L.) Merr.). J. Agric. Food Chem. 2001, 49, 5848-5851.*
Snodgrass, W. Herbal Products: Risks and Benefits of Use in Children. Curr. Therap. Res., 62, 10, 2001, pp. 724-737.*
Hoon Jang et al., "The Changes of Testis and the Effects of Anthocyanin on Spermatogenesis in Rat induced Varicocele", Korean Society for Sexual Medicine and Andrology, Apr. 9, 2011.
Hoon Jang et al., "The Changes of Testis and the Effects of Anthocyanin on Spermatogenesis in Rat induced Varicocele", Korean J Andrology, Apr. 2011, vol. 29, No. 1.
Hoon Jang et al., "The effects of anthocyanin on a rat model of varicocele", The Korean Urological Congree and Expo; KUCE 2011, Apr. 13-14, 2011, BEXCO, Busan.
Hoon Jang et al., "The Changes of Testis and the Effects of Anthocyanin on Spermatogenesis in Rat induced Varicocele", APPSSAM 2011, 6th Congress of Asia Pacific Society for the study of Aging Male, Sep. 1-4, 2011, Paradise Hotel, Busan.
Hoon Jang et al., "Anthocyanin Extracted from Black Soybean Reduces Prostate Weight and Promotes Apoptosis in the Prostatic Hyperplasia-Induced Rat Model", Journal of Agricultural and Food Chemistry. 2010, 58, 12686-12691.
Sun-Hee Kim et al., "A Major Antioxidative Components and Comparison of Antioxidative Activities in Black Soybean," Korean J. Food Sci. Technol. vol. 37, No. 1, pp. 73-77 (Feb. 2005).
Benjamin N. Hendin et al, "Varicocele is associated with elevated spermatozoal reactive oxygen species production and diminished seminal plasma antioxidant capacity," The Journal of Urology, vol. 161, pp. 1831-1834, (Jun. 1999).

* cited by examiner

*Primary Examiner* — Shaojia Anna Jiang
*Assistant Examiner* — Dale R Miller
(74) *Attorney, Agent, or Firm* — Lexyoume IP Meister, PLLC

(57) ABSTRACT

The present invention relates to the therapeutic or ameliorating effects of anthocyanin extracted from black soybean on varicocele or male infertility. In particular, the present invention relates to a method for treating or ameliorating varicocele or male infertility using anthocyanin extracted from black soybean.

2 Claims, 2 Drawing Sheets
(2 of 2 Drawing Sheet(s) Filed in Color)

US 8,980,847 B2

METHOD FOR TREATING VARICOCELE OR MALE INFERTILITY USING ANTHOCYANIN EXTRACTED FROM BLACK SOYBEAN

CROSS REFERENCE TO RELATED APPLICATION

This application claims priority to and the benefit of Korean Patent Application No. 10-2011-0099358 filed on Sep. 29, 2011, which is hereby incorporated by reference for all purposes as if fully set forth herein.

BACKGROUND OF THE INVENTION (a) Field of the Invention

The present invention relates to the therapeutic or ameliorating effects of anthocyanin extracted from black soybean on varicocele or male infertility. In particular, the present invention relates to a method for treating or ameliorating varicocele or male infertility using anthocyanin extracted from black soybean.

(b) Description of the Related Art

Varicocele is the stretching and twisting of the pampiniform plexus of the spermatic cord through which venous blood flows in from the testis, and it is known to be the most common disease underlying male infertility. About 98% of varicocele occur on the left side, because the longer left testicular vein connects to the left renal vein with 90-degree angle, while the right testicular vein drains at less than 90-degrees directly into the significantly lager inferior vena cava. It is detected in approximately 15% of young males. In adults, it is asymptomatic in most cases; nonetheless, it has been reported to account for 35% of primary male infertility and 81% of secondary male infertility.

Until now, the treatments for male infertility caused by varicocele have included risky laparotomies or laparoscopic surgeries and procedures that occlude the expanded pampiniform plexus by angiogram. With the use of these techniques, improvements in the results of postsurgical semen analysis and an increase in the pregnancy rate have been reported. However, these surgical procedures could impose a heavy burden on the patients, and thus there is a need to develop effective drug therapy that can be more easily applied.

In this regard, studies of the mechanisms of abnormal spermatogenesis and infertility have suggested a reduction in gonadotropin or testosterone formation, increased scrotal temperature, apoptosis, reactive oxygen species, and ischemic changes caused by hypoxia as possible mechanisms inducing injury to the testis, but association of varicocele with male fertility has not yet been elucidated. Therefore, there are difficulties in developing effective drugs for varicocele or male infertility caused thereby.

Meanwhile, it is known that black soybeans contain essential fatty acids, lecithin, fiber, saponin or the like so that they have the effect of preventing and treating adult diseases such as hypertension, diabetes, arteriosclerosis, and obesity. The vegetable fiber contained in black soybeans is known to have the effect to prevent not only constipation but also colon cancer. Donguibogam describes black soybeans as "a drug that protects the five viscera, keeps intestines warm by helping twelve meridians, gets rid of boils, and treats radiating pain".

Further, anthocyanin, a pigment contained in black soybeans, is a water-soluble pigment glucoside and known to have antioxidant, anti-aging and antibacterial effects. Anthocyanin is largely divided into six kinds of anthocyanidins depending on the number of the hydroxyl groups and the methylation of specific hydroxyl groups, and also divided into hundreds of kinds depending on the sort of sugar, which binds with anthocyanidins, and the sort and bonding location of the acyl group. It was recently found that each anthocyanin has slightly different bioactivities.

With regard to the medicinal use of anthocyanin extracted from black soybean, Korean Patent No. 10-0832240 provides the use of anthocyanin extracted from black soybean coat for the treatment of wound healing, and Korean Patent No. 10-0785466 provides the use of anthocyanin extracted from black soybean for the treatment of arteriosclerosis and heart diseases by suppressing NF-kB activation and myocardial necrosis after ischemia and reperfusion. In addition, Korean Patent No. 10-0880876 provides the use of anthocyanin extracted from black soybean coat for the treatment of skin flap or ischemia and reperfusion injury, and Korean Patent No. 10-2010-0127017 provides the use thereof for the treatment of diabetes. However, there are no reports about medical effects of anthocyanin extracted from black soybean on varicocele or male infertility in the prior publications including the above publications.

Accordingly, the present inventors have made many efforts to develop therapeutic agents effective for varicocele and male infertility caused thereby. As a result, they found that anthocyanin, extracted from black soybean seed coat, improves testis volume and spermatogenic cell density in a rat model of varicocele; prevents the apoptosis, leading to a reduction in the number of apoptotic bodies; and reduces oxidative stress, leading to a reduction in oxidative injury of DNA in testis tissues. Therefore, they demonstrated that anthocyanin, extracted from black soybean seed coat, is effective for making healthy sperm and furthermore useful for the treatment of varicocele and male infertility, thereby completing the present invention.

SUMMARY OF THE INVENTION

The present invention provides anthocyanin extracted from black soybean for the prevention and treatment of varicocele or male infertility.

Therefore, an object of the present invention is to provide a method for treating varicocele or male infertility, comprising the step of administering an effective amount of a composition comprising delphinidin-3-O-glucoside, cyanidin-3-glucoside, and petunidin-3-O-glucoside into a subject.

Another object of the present invention is to provide a method for treating varicocele or male infertility, comprising the step of administering an effective amount of a composition comprising the anthocyanin-containing black soybean extract into a subject.

Still another object of the present invention is to provide a method for ameliorating varicocele or male infertility, comprising the step of feeding a functional health food comprising delphinidin-3-O-glucoside, cyanidin-3-glucoside, and petunidin-3-O-glucoside into a subject.

Still another object of the present invention is to provide a method for ameliorating varicocele or male infertility, comprising the step of feeding a functional health food comprising the anthocyanin-containing black soybean extract into a subject.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Figure 1:
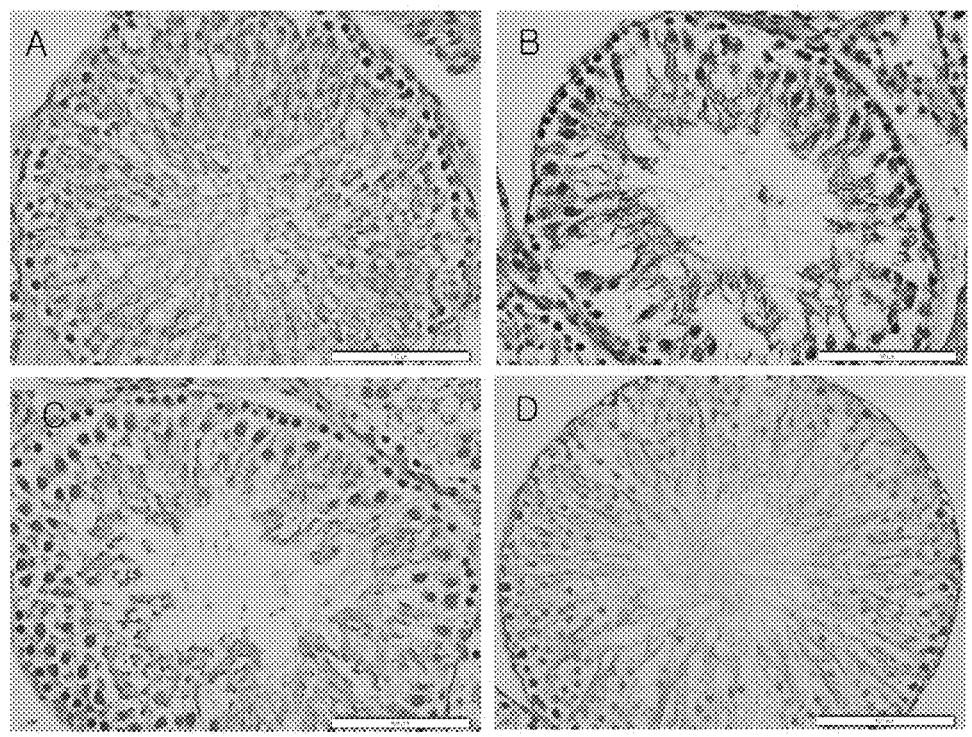
FIG. 1 shows histopathologic findings of left testis by Hematoxylin-Eosin staining, in which (A) represents a normal control group, (B) represents a varicocele-induced group, (C) represents a 40 mg/kg anthocyanin-administered group, and (D) represents an 80 mg/kg anthocyanin-administered group.

In one aspect to achieve the above objects, the present invention relates to a method for treating varicocele or male infertility, comprising the step of administering an effective amount of a composition comprising delphinidin-3-O-glucoside, cyanidin-3-glucoside, and petunidin-3-O-glucoside into a subject.

Preferably, the anthocyanin may be extracted and isolated from black soybean. More preferably, the anthocyanin may be extracted and isolated from black soybean seed coat, but is not limited thereto.

Further, the active ingredients of the present invention, delphinidin-3-O-glucoside, cyanidin-3-glucoside, and petunidin-3-O-glucoside are contained in black soybean in a large amount, and thus the anthocyanin-containing black soybean extract can be also used for the prevention or treatment of varicocele or male infertility.

In another embodiment, the present invention relates to a method for treating varicocele or male infertility, comprising the step of administering an effective amount of a composition comprising the black soybean extract into a subject.

Any type of the black soybean can be included in the scope of the present invention without particular limitation, as long as it contains a large amount of delphinidin-3-O-glucoside, cyanidin-3-glucoside, and petunidin-3-O-glucoside.

Preferably, the composition of the present invention may include 15 to 35% by weight of delphinidin-3-O-glucoside, 55 to 75% by weight of cyanidin-3-glucoside, and 1 to 10% by weight of petunidin-3-O-glucoside.

More preferably, the composition of the present invention may include 10 to 30% by weight of delphinidin-3-O-glucoside, 60 to 70% by weight of cyanidin-3-glucoside, and 3 to 10% by weight of petunidin-3-O-glucoside.

Any extraction method and extraction solvent may be included in the scope of the present invention without limitation, as long as the black soybean extract of the present invention contains delphinidin-3-O-glucoside, cyanidin-3-glucoside, and petunidin-3-O-glucoside. Preferably, the black soybean extract of the present invention is understood to include an extract prepared by extracting the black soybean or black soybean seed coat using a solvent selected from the group consisting of water, C3 to C5 ketones, and C1 to C4 linear or branched alcohols, and mixtures thereof, and an extract prepared by fractionating the extract using one or more selected from the group consisting of water, C5 to C7 alkanes, C1 to C4 linear or branched alcohols, methylene chloride, and ethyl acetate. The preferred extraction solvent is water or ethanol.

The black soybean extract of the present invention may be prepared according to the typical preparation methods of plant extracts, and preferably prepared by hot water extraction, pressure extraction, reflux extraction, warm immersion extraction, ultrasonic extraction or the like, but the method is not limited thereto. In addition, the extract prepared as above may be concentrated or the solvent may be removed therefrom by performing filtration under reduced pressure or by further performing concentration and/or freeze-drying. Therefore, the term "black soybean extract", as used herein, includes a dry extract that is dried by the typical method and a liquid extract or solid extract that is concentrated by removing the extraction solvent.

The term "varicocele", as used herein, refers to a condition of enlarged, twisted veins in the scrotum, and it is known to cause abnormal spermatogenesis and infertility. Thus, the composition of the present invention may be used for a subject having varicocele or male infertility caused thereby.

The prophylactic or therapeutic activities of the composition of the present invention on varicocele or male infertility caused thereby have been directly demonstrated in a rat model of varicocele.

In the specific Example of the present invention, the varicocele-induced animal model showed a statistically significant reduction in the weight of the left testis and spermatogenic cell density, as compared with a normal control group. Because the reduction of testis volume in varicocele patients is an indication of treatment, the reduction of testis volume and the decrease in spermatogenic cell density observed in the present experimental model are thought to be due to the testis injury caused by the varicocele. Furthermore, cells positive for TUNEL, or in other words, apoptotic bodies, were increased in the left testis of the varicocele-induced group, as compared with the normal control group. In the present invention, 8-hydroxy-2'-deoxyguanosine (8-OHdG) was used as a marker of oxidative injury of DNA of testis tissues, and 8-OHdG measured in the left testis of the varicocele-induced group was significantly increased compared with the normal control group, which is thought to be caused by varicocele-induced oxidative injury to sperm DNA.

However, the increase in the testis weight and spermatogenic cell density, and the reduction in the number of apoptotic bodies and 8-OHdG concentration in the testis tissue were observed in the varicocele-induced group that was orally administered with 80 mg/kg of anthocyanin, as compared with the varicocele-induced group. Therefore, it can be seen that the active ingredient of the present invention, the anthocyanin extracted from black soybean seed coat protects the testis tissue against apoptosis and prevents oxidative stress, thereby being used for normal spermatogenesis and for the treatment of varicocele.

As described above, the present invention has first demonstrated that anthocyanin extracted from black soybean minimizes apoptosis of the testis tissue in a rat model of varicocele, and protects against oxidative stress, thereby contributing to the amelioration of varicocele and normal spermatogenesis.

The composition of the present invention may further include nutrients, vitamins, electrolytes, a flavoring agent, a coloring agent, an extender, pectic acid and salts thereof, alginic acid and salts thereof, organic acid, a protective colloid thickener, a PH adjuster, a stabilizer, a preservative, glycerin, alcohol, a carbonating agent used for a carbonated drink, in addition to the active ingredient anthocyanin or the black soybean extract including the same. These ingredients may be added singly or in combination. Preferably, the content of the additional ingredient ranges from 0.1 to 20% by weight based on 100% by weight of anthocyanin or the black soybean extract including the same, or ranges from 100 to 10,000,000% by weight based on 100% by weight of licoricidin, but is not limited thereto.

The content of the anthocyanin or black soybean extract in the composition may be properly adjusted depending on disease severity, symptom progression, patient's status, etc. For example, the content is 0.0001 to 99.9% by weight, preferably 0.001 to 50% by weight, based on the total weight of the composition, but is not limited thereto. The content is based on the solvent-removed dry weight.

The composition may further include an adequate carrier, excipient or diluent commonly used for the preparation of pharmaceutical compositions, and it may be prepared into oral preparations such as powder, granule, tablet, capsule, suspension, emulsion, syrup, aerosol or the like, and preparations for external application, suppository or sterile injection solution according to common methods.

When the composition is formulated, a commonly used diluent or excipient such as filler, extender, binder, wetting agent, disintegrant, surfactant or the like may be used. Solid formulations for oral administration include tablet, pill, powder, granule, capsule or the like, and these solid formulations may include at least one excipient and/or lubricant. Liquid formulations for oral administration include suspension, liquid for internal use, emulsion, syrup or the like, and various excipients such as wetting agent, sweetener, aromatic, preservative or the like may be included, in addition to a commonly used simple diluent such as water and liquid paraffin. Formulations for parenteral administration include sterile aqueous solution, non-aqueous solution, suspension, emulsion, lyophilized preparation and suppository.

A preferred administration dose of the composition varies depending on the patient's physical conditions and body weight, severity of disease, formulation type, administration route and administration period, and may be determined adequately by those skilled in the art. To attain more desirable effect, the composition of the present invention may be administered at a daily dosage of 0.1 to 100 mg/kg based on the active ingredient, but is not limited thereto. The administration may be performed once or several times a day. The composition of the present invention may be administered to animals, preferably mammals including human, via various routes. All administration routes may be contemplated, for example, oral, intravenous, intramuscular, and subcutaneous routes. In pharmaceutical dosage form, the composition of the present invention may be administered in the form of pharmaceutically acceptable salts thereof, or it may be also used alone or in appropriate association, as well as in combination with other pharmaceutically active compounds.

In still another aspect, the present invention relates to a method for ameliorating varicocele or male infertility, comprising the step of feeding a functional health food comprising the anthocyanin extracted from black soybean into a subject.

Preferably, the functional health food includes delphinidin-3-O-glucoside, cyanidin-3-glucoside, and petunidin-3-O-glucoside. More preferably, the composition may include 15 to 35% by weight of delphinidin-3-O-glucoside, 55 to 75% by weight of cyanidin-3-glucoside, and 1 to 10% by weight of petunidin-3-O-glucoside.

In still another aspect, the present invention relates to a method for ameliorating varicocele or male infertility, comprising the step of feeding a functional health food comprising the anthocyanin-containing black soybean extract into a subject.

As used herein, the food means any natural or synthetic product containing one or more nutrients, and preferably those processed to be edible, and it commonly includes a variety of foods, functional health foods, beverages, food additives, and beverage additives. Examples of the food include various foods, beverages, gum, tea, vitamin complex, and functional health foods. Additionally, the food of the present invention includes special nutrient foods (e.g., formula milk, foods for infants and young children, etc.), meat products, fish products, bean curds, curds, noodles (e.g., instant noodle, other noodles, etc.), health food supplements, seasoning foods (e.g., soy sauce, soybean paste, hot pepper paste, mixed soybean paste, etc.), sauces, snacks, dairy products (e.g., fermented milk products, cheese, etc.), other processed foods, kimchi, preserved food products (e.g., kimchi, sliced vegetables preserved in soy sauce, etc.), beverages (e.g., fruit beverages, vegetable beverages, soy milk, fermented beverages, ice cream, etc.), natural seasoning (e.g., instant noodle base, etc.), vitamin complex, alcoholic beverages, liquor, and other health food supplements, but is not limited thereto. The functional health foods, beverages, food additives, or beverage additives may be prepared by the typical method.

The functional health food may include a sitologically acceptable food additive, and further include an adequate carrier, excipient or diluent commonly used for the preparation of functional foods.

Further, the food may include 0.00001% by weight to 50% by weight of the anthocyanin or black soybean extract, based on the total weight of the food, and if the food is a beverage, it may include 0.001 g to 50 g, and preferably 0.01 g to 10 g thereof, based on 100 ml of the food, but is not limited thereto.

Hereinafter, the present invention will be described in detail with reference to Examples. However, these Examples are for illustrative purposes only, and the invention is not intended to be limited by these Examples.

Example 1

Preparation of Materials 1-1. Extraction and Ingredient Analysis of Anthocyanin

The black soybean used in the present experiments was supplied by the Rural Development Administration, and its extraction and ingredient analysis were performed by the same methods used in the previous study of the present inventors (Jang H. et al., J Agric Food Chem 58:12686-91, 2010). The seed coats of black soybean (Chungja 3) were peeled manually, and 500 g thereof were extracted using 2000 ml of 80% ethanol (0.1% acetic acid) at 4° C. for 2 days twice. The solution extract was filtered through a 0.45 um filter, and concentrated using a rotary vacuum evaporator (35° C.) to obtain a crude anthocyanin extract. The residual solvent was removed from the crude extract by freeze-drying, and the resulting red powder was stored at −70°.

HPLC (High performance liquid chromatography) was performed using a Dionex Ultimate 3000 series (Dionex Softron GmbH, Germering, Germany) to analyze the ingredients of the extract of black soybean seed coat. As a result, it was found to include delphinidin-3-O-glucoside (Dp3glc), cyanidin-3-glucoside (Cy3glc), and petunidin-3-O-glucoside (Pt3glc), and the composition of each ingredient is as follows (Table 1).

TABLE 1

| | Anthocyanin content (variety: Chungja 3) | | | |
| --- | --- | --- | --- | --- |
| | Dp3glc | Cy3glc | Pt3glc | Total |
| ug/g | 3049.0 | 8277.2 | 791.7 | 12117.9 |
| wt % | 25.2 | 68.3 | 6.5 | 100 |

1-2. Experimental Animals and Maintenance Condition

Experimental animals were 12-week-old male white Sprague-Dawley rats, weighing 380-400 g, provided by Samtako Bio Korea, Inc., Osan, Korea. After a 1-week acclimation period, the animals were maintained as 2 animals per plastic cage. Animal rooms were controlled by artificial lights for 12 hours from 07:00 to 19:00. Room temperature was 18-23° C. and 40% to 60% humidity was maintained. Animals were allowed to freely access purified water and animal feed. The present experiment was approved by the Institutional Animal Care and Use Committee of the Catholic University of Korea (IRB approval no. CUMC-2010-0106-02).

1-3. Preparation of Normal Control Group and Varicocele-Induced Group

Experimental animals were divided into the normal control group (n=6) and the varicocele-induced group (n=6). Varicocele was induced by partial occlusion of the left renal vein proximal to the entry of the testicular vein according to the method of Saypol et al. (Saypol D C, et al., J Clin Invest 68:39-45, 1981). A 8 mm plastic probe was attached in parallel to the left renal vein, and the vein was sutured with 3.0 silk, and the plastic probe was removed.

1-4. Preparation of Anthocyanin-Administrated Group

Immediately after the induction of varicocele, the anthocyanin-administrated group (n=12) was divided into two subgroups; the first group (n=6) was orally administered with 40 mg/kg of anthocyanin, and the second group (n=6) was orally administered with 80 mg/kg of anthocyanin. The anthocyanin-administrated groups were orally administered with the extract of black bean seed coat diluted in distilled water at a dose of 40 mg/kg or 80 mg/kg per weight of white rat once a day for 4 weeks.

Example 2

Collection of Testis Tissues and Measurement of Spermatogenic Cell Density

After 4 weeks, animals were anesthetized, both testes were resected by lower abdominal resection, and the testis weight was measured. Tissues were then obtained, fixed in 10% neutral formalin, embedded in paraffin, stained with Hematoxylin-Eosin, and examined under an optical microscope. Under an optical microscope at 400× magnification, 10 sites of seminiferous tubules that were almost round were selected randomly, and the spermatogenic cell density was obtained by measuring the thickness of the germinal cell layer and the diameter of the seminiferous tubules.

Example 3

Collection and Evaluation of Cauda Epididymal Spermatozoa

Cauda epididymides were minced in 5 ml of normal saline containing 0.5% bovine serum albumin at 37° C. and were then filtered. Sperm suspensions were placed on glass slides that had been pre-warmed at 37° C. Percentages of motile sperm were determined by counting more than 200 spermatozoa in randomly selected fields under an optical microscope. Sperm counts were expressed as the number of motile spermatozoa per gram of cauda epididymis tissue (Kim, S. J., et al., Korean J Urol 33, 404-417, 1992). Samples were evaluated by one expert investigator unaware of sample identities.

Example 4

TUNEL (Terminal Dexoynucleotidyl Transferase Mediated dUTP Nick End Labeling) Assay and Apoptosis Assessment To assess apoptosis in the extracted testis tissues, TUNEL assay was performed by use of Apop Tag In Situ Apoptosis Detection Kits (Millipore Co., Massachusetts, US). For assessment of apoptosis in the testis tissue, the number of cells positive for the TUNEL assay was counted and the difference among the groups was assessed. For the count of cells positive for TUNEL assay, 10 sites were selected randomly from a slide of each group, and the number of cells positive for TUNEL assay was counted under an optical microscope at 200× magnification.

Example 5

Measurement of Oxidative Stress

Oxidative stress in testis tissues was evaluated by quantifying the levels of 8-hydroxy-2'-deoxyguanosine (8-OHdG) as oxidatively modified DNA. By use of the DNeasy Blood & Tissue kit (Qiagen, Valencia, Calif.), total DNA was extracted from the testis, and the 8-OHdG levels were measured with a DNA oxidation kit (Highly Sensitive 8-OHdG Check ELISA; Japan Institute for the Control of Aging, Fukuroi, Japan). The 8-OHdG standard (0.5-40 ng/mL) or DNA (15~20 ug) purified from the testis was incubated for 1 hour with a monoclonal antibody against 8-OHdG in a microtiter plate pre-coated with 8-OHdG. After the addition of 3,3',5,5'-tetramethylbenzidine, absorbance was measured at 450 nm. Tissue sample concentration was calculated from a standard curve, and was corrected for DNA concentration.

Example 6

Statistical Analysis

The measured values are presented as the mean±standard deviation. For statistical analysis, SPSS for Microsoft Windows (ver. 12.0) was used. Statistical analysis was performed by the application of the Kruskal-Wallis test and the Mann-Whitney U-test. For comparison of the groups, Tukey's test was performed, and p values less than 0.05 were determined to be statistically significant.

Results

1. Testis Weigh

Mean weights of left testis are shown in Table 2. Compared with normal control group, the average left testis weight of varicocele-induced group showed a statistically significant reduction (p<0.05). There was no significant difference (p>0.05) in the weight of left testis between the varicocele-induced group and the group administered with 40 mg/kg of anthocyanin. In the group administered with 80 mg/kg of anthocyanin, however, the weight of the left testis was significantly increased compared with the varicocele-induced group (p<0.05).

TABLE 2

|  | Weight of left testis (g) |
| --- | --- |
| Normal control group | 1.858 ± 0.125 |
| Varicocele-induced group | 1.475 ± 0.04 |
| 40 mg/kg anthocyanin-administered group | 1.628 ± 0.042 |
| 80 mg/kg anthocyanin-administered group | 1.818 ± 0.025 |

2. Sperm Counts and Motility

The mean sperm counts and percentages of motile spermatozoa in the left epididymis are shown in Table 3. The sperm count in each group showed no statistically significant differences ($p>0.05$). Although there was no significant difference ($p>0.05$) in sperm motility between the varicocele-induced group and the group administered with 40 mg/kg of anthocyanin, a statistically significant difference ($p<0.05$) was shown in the normal control and the group administered with 80 mg/kg of anthocyanin, compared with the varicocele-induced group.

TABLE 3

|  | Sperm count of left epididymis ($\times 10^6$/g of cauda) | Sperm motility of left epididymis (percentages of motile spermatozoa) |
| --- | --- | --- |
| Normal control group | 259.1 ± 17.8 | 78.7 ± 2.9 |
| Varicocele-induced group | 213.7 ± 11.5 | 55.9 ± 2.7 |
| 40 mg/kg anthocyanin-administered group | 231.2 ± 27.3 | 62.9 ± 1.3 |
| 80 mg/kg anthocyanin-administered group | 245.9 ± 12.4 | 74.9 ± 2.3 |

3. Spermatogenic Cell Density (Thickness of the Germinal Cell Layer/Diameter of Seminiferous Tubules)

In the normal control group, several layers of spermatocytes formed the germinal cell layer. In the varicocele-induced group, however, spermatocytes were decreased and necrosis was observed in the germinal cell layer. In the anthocyanin-administered group, the spermatocyte count and germinal cell layer thickness were higher than those of the varicocele-induced group. Especially, in the group administered with 80 mg/kg of anthocyanin, the germinal cell layer was thicker than that of the varicocele-induced group and was arranged equally, just like in the normal control group (FIG. 1).

The spermatogenic cell density of left testis is shown in Table 4. Compared with the normal control group, the spermatogenic cell density of the varicocele-induced group was significantly decreased ($p<0.05$). There was no statistically significant difference in spermatogenic cell density between the varicocele-induced group and the group administered with 40 mg/kg of anthocyanin ($p>0.05$). In the group administered with 80 mg/kg of anthocyanin, however, the spermatogenic cell density of the left testis was significantly increased, compared with the varicocele-induced group ($p<0.05$).

TABLE 4

|  | Spermatogenic cell density (thickness of the germinal cell layer/diameter of seminiferous tubules) |
| --- | --- |
| Normal control group | 0.342 ± 0.027 |
| Varicocele-induced group | 0.274 ± 0.048 |
| 40 mg/kg anthocyanin-administered group | 0.312 ± 0.046 |
| 80 mg/kg anthocyanin-administered group | 0.345 ± 0.042 |

4. Assessment of Apoptosis and Evaluation

Figure 2:
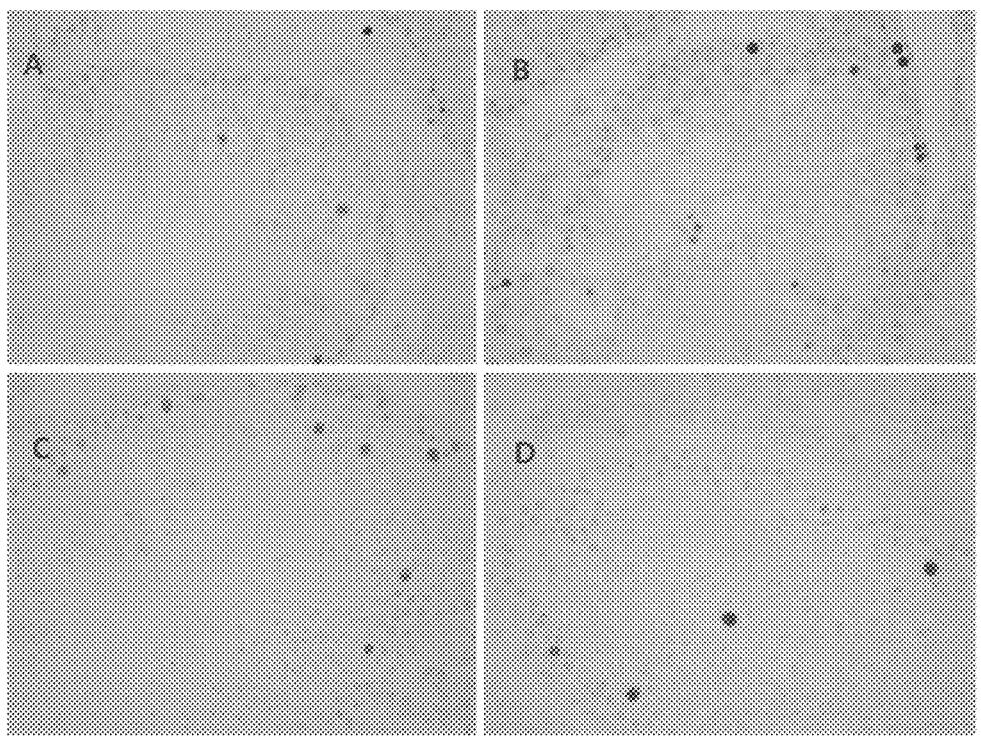
FIG. 2 shows apoptotic bodies in TUNEL staining of left testis, in which (A) represents a normal control group, (B) represents a varicocele-induced group, (C) represents a 40 mg/kg anthocyanin-administered group, and (D) represents an 80 mg/kg anthocyanin-administered group.

As shown in FIG. 2, cells undergoing apoptosis form cellular apoptotic bodies, which in the TUNEL assay are observed to be black or dark brown in color (FIG. 2). The varicocele-induced group showed the higher number of apoptotic bodies than the normal control group ($p<0.05$). In 40 mg/kg anthocyanin-administered group and 80 mg/kg anthocyanin-administered group, the number of apoptotic bodies was significantly reduced compared to the varicocele-induced group ($p<0.05$).

The number of apoptotic bodies in the left testis is shown in Table 5. Compared with the varicocele-induced group, significantly fewer cells were stained positively in the TUNEL assay in the normal control group and anthocyanin-administrated groups ($p<0.05$).

TABLE 5

|  | Number of apoptotic bodies in left testis (n) |
| --- | --- |
| Normal control group | 4.93 ± 1.10 |
| Varicocele-induced group | 15.63 ± 8.30 |
| 40 mg/kg anthocyanin-administered group | 8.85 ± 2.55 |
| 80 mg/kg anthocyanin-administered group | 6.23 ± 0.43 |

5. Measurement of Oxidative Stress in Testis Tissues

Oxidative stress in the testis tissues was assessed quantitatively by measuring 8-OHdG in the testis by ELISA. The concentration of 8-OHdG in left testis is shown in Table 6. A significant increase in oxidative stress was shown in the varicocele-induced group, compared with the normal control group ($p<0.05$). There was no statistically significant difference between the varicocele-induced group and the group administered with 40 mg/kg of anthocyanin ($p>0.05$). However, the group administered with 80 mg/kg of anthocyanin showed a statistically significant reduction in oxidative stress, compared with the varicocele-induced group ($p<0.05$).

TABLE 6

|  | 8-OHdG concentration in left testis (ng/ml) |
| --- | --- |
| Normal control group | 0.719 ± 0.107 |
| Varicocele-induced group | 1.526 ± 0.257 |
| 40 mg/kg anthocyanin-administered group | 1.087 ± 0.199 |
| 80 mg/kg anthocyanin-administered group | 0.585 ± 0.161 |

EFFECT OF THE INVENTION

The composition of the present invention, comprising anthocyanin extracted from black soybean, improves testis volume and spermatogenic cell density; prevents the apoptosis, leading to a reduction in the number of apoptotic bodies; and reduces oxidative stress, leading to a reduction in oxidative injury of DNA in testis tissues. Therefore, the composition is effective for making healthy sperm, and furthermore useful for the treatment of varicocele and male infertility.

What is claimed is:

1. A method for treating infertile varicocele, the method comprising the step of administering into a subject, in need thereof, an effective amount of a composition consisting of 15 to 35% by weight of delphinidin-3-O-glucoside, 55 to 75% by weight of cyanidin-3-glucoside, 1 to 10% by weight of petunidin-3-O-glucoside, and a pharmaceutically acceptable carrier.

2. A method for ameliorating infertile varicocele, the method comprising the step of feeding into a subject, in need thereof, a functional health food consisting of 15 to 35% by weight of delphinidin-3-O-glucoside, 55 to 75% by weight of cyanidin-3-glucoside, 1 to 10% by weight of petunidin-3-O-glucoside, and a sitologically acceptable food additive.

* * * * *